(12) United States Patent
Taubman et al.

(10) Patent No.: US 9,236,709 B2
(45) Date of Patent: Jan. 12, 2016

(54) CHEMICAL DETECTION AND LASER WAVELENGTH STABILIZATION EMPLOYING SPECTROSCOPIC ABSORPTION VIA LASER COMPLIANCE VOLTAGE SENSING

(71) Applicants: Matthew S. Taubman, West Richland, WA (US); Mark C. Phillips, Kennewick, WA (US)

(72) Inventors: Matthew S. Taubman, West Richland, WA (US); Mark C. Phillips, Kennewick, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 3 days.

(21) Appl. No.: 14/153,853

(22) Filed: Jan. 13, 2014

(65) Prior Publication Data

US 2014/0226686 A1    Aug. 14, 2014

Related U.S. Application Data

(62) Division of application No. 13/566,783, filed on Aug. 3, 2012, now Pat. No. 8,675,696.

(60) Provisional application No. 61/592,297, filed on Jan. 30, 2012, provisional application No. 61/653,991, filed on May 31, 2012.

(51) Int. Cl.
| | |
|---|---|
| *H01S 3/10* | (2006.01) |
| *H01S 5/068* | (2006.01) |
| *G01N 21/39* | (2006.01) |
| *H01S 5/00* | (2006.01) |
| *H01S 5/14* | (2006.01) |
| *H01S 5/34* | (2006.01) |
| *G01N 21/03* | (2006.01) |

(Continued)

(52) U.S. Cl.
CPC ............ *H01S 5/06808* (2013.01); *G01N 21/39* (2013.01); *H01S 5/0028* (2013.01); *H01S 5/143* (2013.01); *H01S 5/3402* (2013.01); *G01N 21/031* (2013.01); *G01N 2021/399* (2013.01); *G01N 2021/7776* (2013.01); *G01N 2201/0612* (2013.01); *H01S 5/0617* (2013.01); *H01S 5/0687* (2013.01); *H01S 5/141* (2013.01); *H01S 5/3401* (2013.01)

(58) Field of Classification Search
CPC ... H01S 5/0687; H01S 5/06808; H01S 5/068; H01S 5/141
USPC ........................ 372/20, 24, 32, 45.01, 102, 97
See application file for complete search history.

(56) References Cited

U.S. PATENT DOCUMENTS

| | | | | |
|---|---|---|---|---|
| 5,691,989 | A * | 11/1997 | Rakuljic et al. | 372/20 |
| 6,205,159 | B1 * | 3/2001 | Sesko et al. | 372/20 |

(Continued)

OTHER PUBLICATIONS

Mitsuhashi, Y., et al., Self-Coupled Optical Pickup, Optics Communications, 17, 1, 1976, 95-97.

(Continued)

*Primary Examiner* — Kinam Park
(74) *Attorney, Agent, or Firm* — James D. Matheson

(57) ABSTRACT

Systems and methods are disclosed that provide a direct indication of the presence and concentration of an analyte within the external cavity of a laser device that employ the compliance voltage across the laser device. The systems can provide stabilization of the laser wavelength. The systems and methods can obviate the need for an external optical detector, an external gas cell, or other sensing region and reduce the complexity and size of the sensing configuration.

10 Claims, 4 Drawing Sheets

(51) Int. Cl.
  *H01S 5/06* (2006.01)
  *H01S 5/0687* (2006.01)
  *G01N 21/77* (2006.01)

(56) References Cited

U.S. PATENT DOCUMENTS

| | | | |
|---|---|---|---|
| 6,611,546 B1* | 8/2003 | Garnache et al. | 372/92 |
| 2002/0015427 A1* | 2/2002 | Pilgrim et al. | 372/20 |
| 2004/0165641 A1* | 8/2004 | Garnache et al. | 372/97 |

OTHER PUBLICATIONS

Mitsuhashi, Y., et al., Voltage Change Across the Self-Coupled Semiconductor Laser, IEEE Journal of Quantum Electronics, QE-17, 7, 1981, 1216-1225.

Rochford, K. B., et al., Simultaneous laser-diode emission and detection for fiber-optic sensor applications, Optics Letters, 20, 20, 2105-2107, Oct. 15, 1995.

Hofstetter, D., et al., Quantum-cascade-laser structures as photodetectors, Applied Physics Letters, 81, 2002, 2683-2685.

Von Staden, J., et al., Measurements of the a factor of a distributed-feedback quantum cascade laser by an optical feedback self-mixing technique, Optics Letters, 31, 17, 2006, 2574-2576.

Belkin, M. A., et al., Intra-cavity absorption spectroscopy with narrow-ridge microfluidic qauantum cascade lasers, Optics Express, 15, 18, 2007, 1-10.

Lim, Y. L., et al., Self-mixing interferometry with a Terahertz Quantum Cascade Laser: feedback induced voltage signal, School of Information Technology and Electrical Engineering, The University of Queensland, Australia, School of Electronic and Electrical Engineering, University of Leeds, UK, IEEE, 2010, 11-12.

Medhi, G., et al., Infrared Intracavity Laser Absorption Spectrometer, Proc. of SPIE, 7680, 2010, 1-8.

Dean, P., et al., Terahertz imaging through self-mixing in a quantum cascade laser, 36, 13, Optics Letters, 2011, 2587-2589.

Lim, Y. L., et al., Demonstration of a self-mixing isplacement sensor based on terahertz quantum cascade lasers, Applied Physics Letters, 99, 2011, 081108-1-081108-3.

Medhi, G., et al., Intracavity laser absorption spectroscopy using mid-IR quantum cascade laser, Proc. of SPIE vol. 8032, 2011, 80320E-1-80320E-7.

Phillips, M. C., et al., Intracavity sensing via compliance voltage in an external cavity quantum cascade laser, Optics Letters, 37, 13, 2012, 2664-2666.

* cited by examiner

CHEMICAL DETECTION AND LASER WAVELENGTH STABILIZATION EMPLOYING SPECTROSCOPIC ABSORPTION VIA LASER COMPLIANCE VOLTAGE SENSING

CROSS REFERENCE TO RELATED APPLICATION

This is a Divisional Application that claims priority from U.S. patent application Ser. No. 13/566,783 filed 3 Aug. 2012, now allowed, which claims priority from U.S. Provisional Patent Application No. 61/592,297 filed 30 Jan. 2012, and U.S. Provisional Patent Application No. 61/653,991 filed 31 May 2012, which references are incorporated herein in their entirety.

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The invention relates generally to laser-based chemical sensors. More particularly, the invention relates to use of an external cavity quantum cascade laser both as a light source and as a chemical detection mechanism. Finally, the invention relates to wavelength stabilization of an external cavity quantum cascade laser.

BACKGROUND OF THE INVENTION

Traditional gas-phase spectroscopic absorption techniques use a laser, a gas cell or interaction region of some kind, and a photodetector to detect the intensity of light passing through the interaction region. Absorbed light at specific wavelengths indicates spectroscopic absorption features of a gaseous species. Photothermal spectroscopy is one conventional technique that employs a pulsed or modulated laser. The emission (beam) from the laser is absorbed by a gaseous analyte in a cell or interaction region that causes local heating within the gas. The heating of the gas changes the refractive index of the gas. The change in the refractive index is then detected (e.g., interferometrically) with a second laser. The second laser need not be the same laser as the first pulsed laser in either power or wavelength. Photoacoustic spectroscopy is another conventional technique in which the emission of a pulsed laser is absorbed by a gaseous analyte in a cell or interaction region that causes acoustic excitation of the surrounding gas. The acoustic excitation of the gas is detected with a microphone. In one variation, the laser emission is passed between the tines of a small turning fork and absorbed by gaseous analytes surrounding the tuning fork. Resulting pulsating pressure changes excite the fundamental mode of the turning fork, causing an electrical signal to be emitted through the electrical connections of the device which are subsequently detected.

Quantum Cascade Lasers (QCLs) are an important light source for chemical detection in the mid infrared (MIR) range (3 to 20 microns) because the emission wavelengths coincide with the fundamental absorption bands of many chemical species of interest. Tunable QCLs, in particular, external cavity QCLs (ECQCLs), are of particular appeal because they represent a single device with a typical tuning range that is 10%, and often up to 20%, of the center wavelength. Thus, only a few ECQCLs are needed to cover large swaths of the MIR. In conventional ECQCL configurations, the ECQCL is used to develop tunable wavelengths as optical outputs. The emission outputs interact with gaseous samples and allow their detection by various detectors (e.g., photodetectors) located external to the ECQCL. Both QCLs and ECQCLs (and other semiconductor lasers) can thus be used in concert with various traditional detection approaches.

However, in all of these approaches, despite the increasing capabilities of the lasers and their various laser configurations, the techniques are limited by the detection limits of the photodetectors and acoustic detectors in the MIR. The present invention addresses this problem by providing improved QCL and ECQCL laser configurations and methods for precise and sensitive detection of analytes without the need of a separate detector.

SUMMARY OF THE PRESENT INVENTION

A method is described for identification and quantitative determination of an analyte or analytes present in an external cavity of an external cavity laser (ECL) by measuring changes in the compliance voltage appearing across a laser device within the ECL. The method may include supplying a drive current to a laser device located within the ECL; setting an operating wavelength of the ECL to a value corresponding to an absorption feature of the analyte or analytes; and measuring the compliance voltage across the laser device to identify the analyte or analytes. The method may also include modulating the drive current to the ECL or modulating the operating wavelength of the ECL, and demodulating the compliance voltage.

A method is also described for identification and quantitative determination of analytes that may include sweeping an operating wavelength of the ECL. The method may include displaying and/or processing the compliance voltage as a function of operating wavelength, which may provide a compliance voltage spectrum. The method may also include modulating the drive current to the ECL or modulating the operating wavelength of the ECL and demodulating the compliance voltage to obtain a demodulated compliance voltage spectrum.

A method is also described for stabilizing an operating wavelength of an external cavity laser (ECL). The method may include: supplying a drive current to a laser device located within the ECL; modulating the operating wavelength of a laser mode of the ECL at a preselected modulation frequency, waveform, and amplitude when an analyte or analytes is present in the external cavity of the ECL; setting an average operating wavelength of the ECL to a value corresponding to an absorption feature of the analyte(s); measuring a compliance voltage developed across the laser device; demodulating the compliance voltage at a preselected demodulation frequency, waveform, and amplitude to obtain an error signal; passing the error signal to a control member; applying an output of the control member to at least one wavelength-selective element within the external cavity of the ECL to form a feedback loop that acts on the operating wavelength of the ECL; and adjusting the gain, phase, and bandwidth of the control member to stabilize the feedback look and the operating wavelength of the ECL.

Sweeping can include a range of wavelengths that encompasses one or more absorption features of the analytes or obtaining a signal corresponding to the at least one absorption feature of the analyte(s). Sweeping may include continuous variation or piece-wise variation over the selected range of wavelengths.

Modulating the operating wavelength and setting the operating wavelength may employ the same wavelength-selective element within the external cavity of the ECL or may employ distinct wavelength-selective elements within the external cavity of the ECL.

Modulating may include a modulation frequency in the range from 0 Hz to 100 GHz.

Demodulating may include a demodulation frequency that is a multiple of the modulation frequency. The multiple may be an integer. The multiple may also be a rational fraction.

Identifying the analyte may include obtaining a corrected compliance voltage by applying a mathematical function to the compliance voltage.

The mathematical function may also be a single-valued mathematical function. The mathematical function may also be a binary mathematical function.

The method may include comparing the compliance voltage to a known value of the compliance voltage to determine the analytes. The compliance voltage may also be compared to a known value of the compliance voltage that is measured in the absence of an analytes. The compliance voltage may also be compared to a known value of the compliance voltage that is measured with a selected concentration of analytes in the ECL.

The demodulation frequency can range from 0 Hz to 100 GHz.

The demodulated compliance voltage may be obtained as a function of the wavelength sweep signal of a wavelength-selective element within the external cavity of the ECL.

Sweeping the operating wavelength may include simultaneously modulating the operating wavelength at a selected frequency, waveform, and amplitude.

Sweeping the operating wavelength can include supplying a sweep signal to a wavelength-selective element located within the external cavity of the ECL.

The wavelength-selective element may be a diffraction grating.

The wavelength-selective element may also be a mirror that acts in concert with a diffraction grating.

The wavelength-selective element may also be a piezo-electric element.

Supplying the drive current to the laser device may include modulating the current at a selected frequency, waveform, and amplitude. The modulation frequency can range from 0 Hz to 100 GHz.

Identifying analytes may also include comparing one or more features of the corrected compliance voltage spectrum with absorption features appearing in a known spectrum or known spectra obtained from a spectral database of known analytes.

Identifying analytes may also include a least squares fit analysis or a weighted least squares fit analysis.

Setting the operating wavelength may include modulating the operating wavelength at a preselected frequency, waveform, and amplitude. The modulation frequency can range from 0 Hz to 100 GHz.

Stabilizing the operating wavelength of the ECL may include: modulating the operating wavelength of a laser mode of the ECL at a selected modulation frequency, waveform, and amplitude when an analyte or analytes is present in the external cavity of the ECL; demodulating a compliance voltage (or signal) developed across the laser device located within the ECL at a selected demodulation frequency, waveform, and amplitude to obtain an error signal; passing the error signal to a control system, member, or device; applying an output of the control system or device to at least one wavelength-selective element within the external cavity of the external cavity laser to adjust the wavelength of the laser mode of the external cavity laser to correspond to at least one absorption feature of the at least one analyte within the external cavity of the external cavity laser to form a feedback loop through the laser mode; and positioning the feedback loop formed through the laser mode on the at least one absorption feature appearing on the compliance voltage of the laser and locking same thereon.

The control system, member, or device may include amplifiers, limiters, servos, servo-controllers, integrators, differentiators, filters, notches, computers, delays, and combinations of these various devices and elements Positioning a feedback loop may include controlling gain and filter parameters of the feedback loop such that the wavelength of the laser mode of the ECL is locked to one or more absorption features of the analytes within the external cavity.

Wavelength-selective elements can include, but are not limited to, e.g., gratings, etalons, piezo-electric elements or devices, and the like.

The range of wavelengths scanned may encompass one or more absorption features of an analyte or analytes to obtain a signal corresponding to the absorption feature of the analytes.

Lasers can include, but are not limited to, e.g., semiconductor lasers, diode lasers, quantum cascade (QC) lasers, inter-band cascade lasers (iCLs), continuous wave (CW) lasers, pulsed lasers, distributed feedback (DFB) quantum cascade (QC) lasers (DFB-QCLs), components thereof, and combinations of these various lasers and laser systems.

Modulating the operating wavelength may include modulating the drive current to the laser device located within the ECL.

Modulating the operating wavelength may also include modulating with at least one wavelength-selective element located within the external cavity of the ECL.

Modulating the operating wavelength and setting the operating wavelength employ the same wavelength-selective element within the external cavity of the ECL.

Modulating the operating wavelength and setting the operating wavelength employ distinct wavelength-selective elements within the external cavity of the ECL.

Positioning the feedback loop may include controlling gain and filter parameters such that the wavelength of the laser mode of the external cavity laser is locked to the at least one absorption feature of the analyte(s) within the external cavity thereof.

Analytes can include gases, liquids, solids, plasmas, and combinations of these various analyte forms.

Analytes may be deliberately introduced or passively introduced into the external cavity of the ECL.

Analytes may also fill the external cavity of the ECL.

Analytes can fill the entire internal volume of the external cavity of the ECL. Analytes may also be contained within a gas cell such as a multipass cell located within the external cavity of the ECL.

Identifying analytes may include introducing a gas cell within the external cavity of the ECL such that the optical path of the ECL passes through the gas cell where analytes in the gas cell can interact with the optical beam circulating within the external cavity of the ECL.

Absorption features including, e.g., spectral or spectroscopic features of the one or more analytes may be within the wavelength tuning range of the ECL.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DETAILED DESCRIPTION

Detailed herein are methods for identification and quantitative determination an analyte or analytes without the need for external detectors or external gas interaction regions. The following description details a best mode of at least one embodiment of the present invention. While the various embodiments described herein involve an external cavity quantum cascade laser (ECQCL), the invention is not intended to be limited thereto. For example, other lasers and laser systems may be employed. Lasers include, but are not limited to, e.g., semiconductor lasers, diode lasers, quantum cascade (QC) lasers, inter-band cascade lasers (iCLs), continuous wave (CW) lasers, distributed feedback (DFB) quantum cascade (QC) lasers (DFB-QCLs), components thereof, and combinations of these various lasers and laser systems. It will also be clear from the description that the invention is susceptible of various modifications and alternative constructions. Thus, it should be understood that there is no intention to limit the invention to the specific forms disclosed, but, on the contrary, the invention is to cover all modifications, alternative constructions, and equivalents falling within the spirit and scope of the invention as defined in the claims. Therefore the present description should be seen as illustrative and not limiting.

Figure 1:
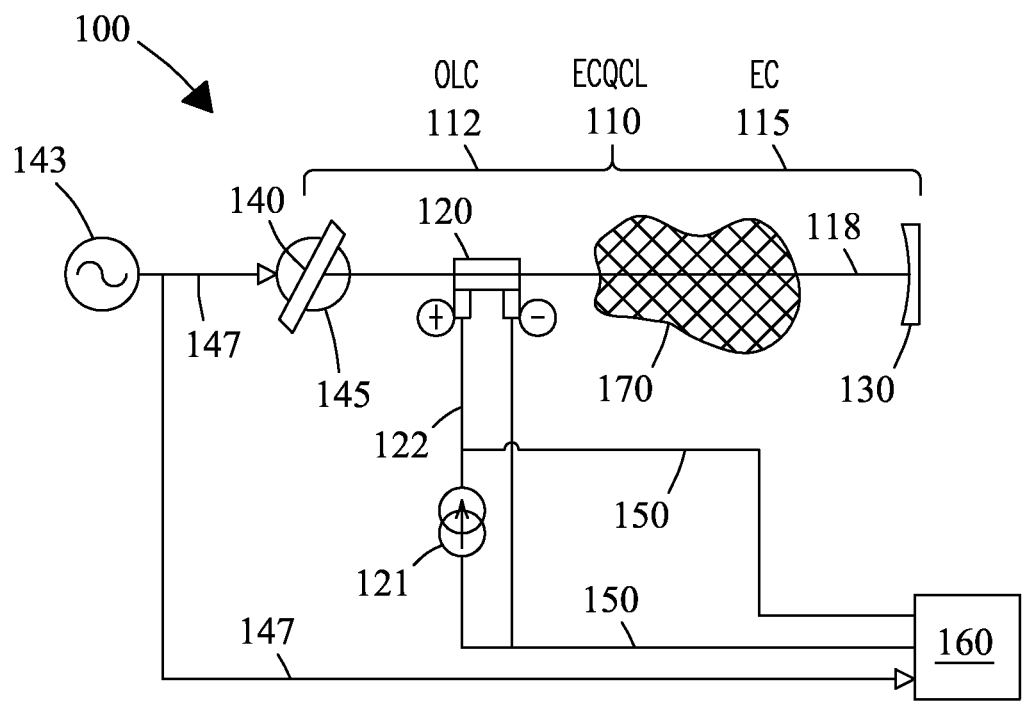
FIG. 1 shows a system that includes an external mirror for direct voltage detection and wavelength scanning in a Littrow ECQCL configuration, according to one embodiment of the invention.

FIG. 1 shows an ECQCL 100 employing compliance voltage measurement for chemical detection, or ECQCL voltage-mediated intra-cavity sensor (EVIS) 100 arranged in a Littrow configuration. The ECQCL may be used both as an optical source and as a chemical detector and/or sensor. Detection of analytes may occur internal to (i.e., within the external cavity of) the ECQCL by monitoring changes in the compliance voltage appearing across the quantum cascade laser (QCL). The voltage appearing across the QCL may be distinct from the current used to drive the QCL device within the ECQCL. And, detection of analytes does not need optical outputs that are delivered from the ECQCL, as detailed herein. For example, EVIS 100 may operate as a chemical sensor incorporated within an optical source. EVIS 100 includes an ECQCL 110 that includes a QCL device 120, an external mirror 130, and a wavelength-selective element or device 140 such as an optical grating, an etalon, or an interferometer. An optical laser cavity (OLC) 112 in which a laser mode or ECQCL mode 118 exists, is defined by these same items: external mirror 130, the QCL device 120, and optical grating 140. The external cavity (EC) 115 is defined as that portion of the optical laser cavity 112 external to the QCL device 120. ECQCL mode 118 is common to both QCL 120 and EC 115. Optical grating 140 may be mounted on an actuator 145 that tunes the wavelength of ECQCL 110. EVIS 100 may also include a signal-generating device 143 that supplies actuator 145 with a scanning signal 147. Scanning signal 147 provides rotation of the grating 140, e.g., in a periodic manner. EVIS 100 may further include a current controller 121, which supplies QCL 120 with current 122. Compliance voltage 150 appearing across QCL 120 (and thus simultaneously across current controller 121) may be monitored with a measurement system 160 that may include amplifiers, mixers, filters, and computers or CPUs, but is not limited thereto. Compliance voltage 150 is preferably recorded simultaneously with scanning signal 147, and displayed with respect to, or processed as a function of, scanning signal 147. Presence of an analyte 170 or multiple analytes 170 in external cavity 115 of ECQCL 110 can be passively introduced by way of their natural presence in ambient air pervading ECQCL 110, or may by deliberately introduced into optical laser cavity 112, e.g., in a gas stream, in a gas sample, or by another means. Analytes 170 in external cavity 115 of ECQCL 110 cause changes to ECQCL optical mode 118, which in turn cause changes in the compliance voltage 150 detected across QCL 120, which changes are detected by measurement system 160. Analytes 170 are thus detected by observing or registering changes in compliance voltage 150.

Figure 2:
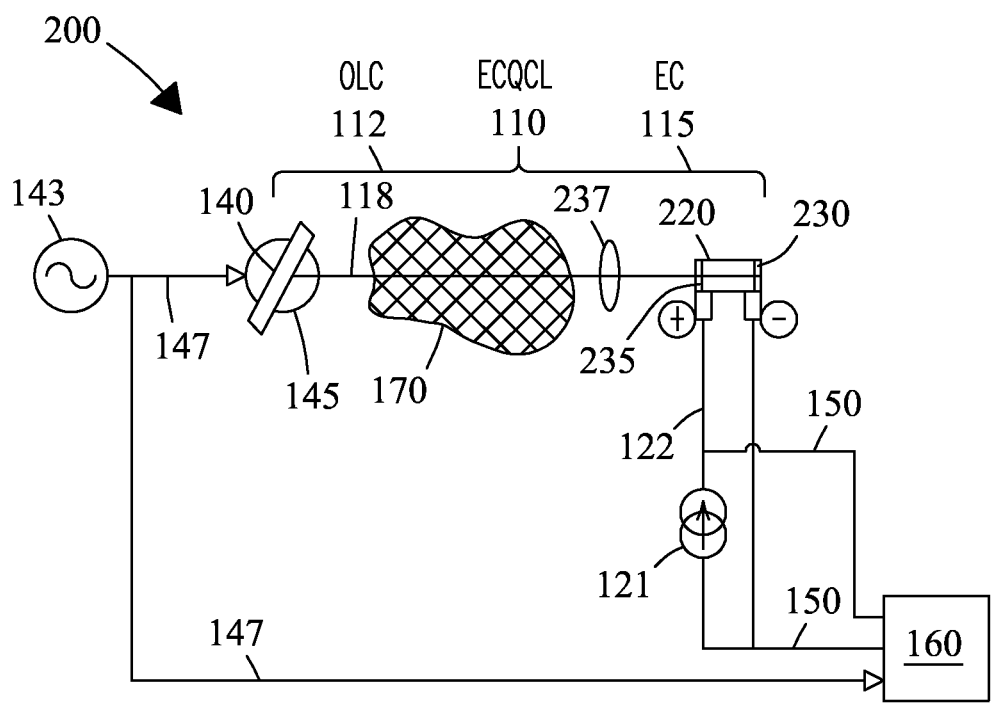
FIG. 2 shows a system that includes a QCL with a high reflectance coating for direct voltage detection and wavelength scanning in a Littrow ECQCL configuration, according another embodiment of the invention.

FIG. 2 shows an ECQCL voltage-mediated intra-cavity sensor (EVIS) 200 arranged in a Littrow configuration. EVIS 200 may operate as a chemical sensor incorporated within an optical source. EVIS 200 includes an ECQCL 110 that includes a QCL device 220 with a high-reflectance mirror coating 230 and anti-reflection coating 235, a focusing lens 237, and a wavelength-selective device (element) 140 such as an optical grating, an etalon, or an interferometer. Optical laser cavity 112 in which an ECQCL mode 118 (or laser mode) exists may be defined by these same items: QCL device 220, and optical grating 140. External cavity (EC) 115 is defined as that part of the laser cavity external to QCL device 220. ECQCL mode 118 is common to both QCL 220 and EC 115. Optical grating 140 may be further mounted on an actuator 145 that tunes the wavelength of ECQCL 110. EVIS 200 may also include a signal-generating device 143 that supplies actuator 145 with a scanning signal 147. Scanning signal 147 may provide rotation of grating 140, e.g., in a periodic manner. EVIS 200 may further include a current controller 121 to supply QCL 220 with current 122. Compliance voltage 150 appearing across QCL 220 (and thus simultaneously across current controller 121) may be monitored with a measurement system 160 including one or more of, but not limited to, e.g., amplifiers, mixers, filters, and a computer or CPU. Compliance voltage 150 is preferably recorded simultaneously with scanning signal 147 and displayed with respect to, or processed as a function of, scanning signal 147. Presence of an analyte 170 or multiple analytes 170 in external cavity 115 of ECQCL 110 can be the result of their natural presence (i.e., passive introduction) in ambient air pervading ECQCL 110, or may be the result of deliberate introduction into optical laser cavity 112, e.g., in a gas stream, in a gas sample, or by another means. Analytes 170 in external cavity 115 of ECQCL 110 may cause changes to ECQCL optical mode 118, which in turn may cause changes in compliance voltage 150 detected across QCL 220 as detected by measurement system 160. Analytes 170 may thus be detected by observing (or registering) changes in compliance voltage 150.

Figure 3:
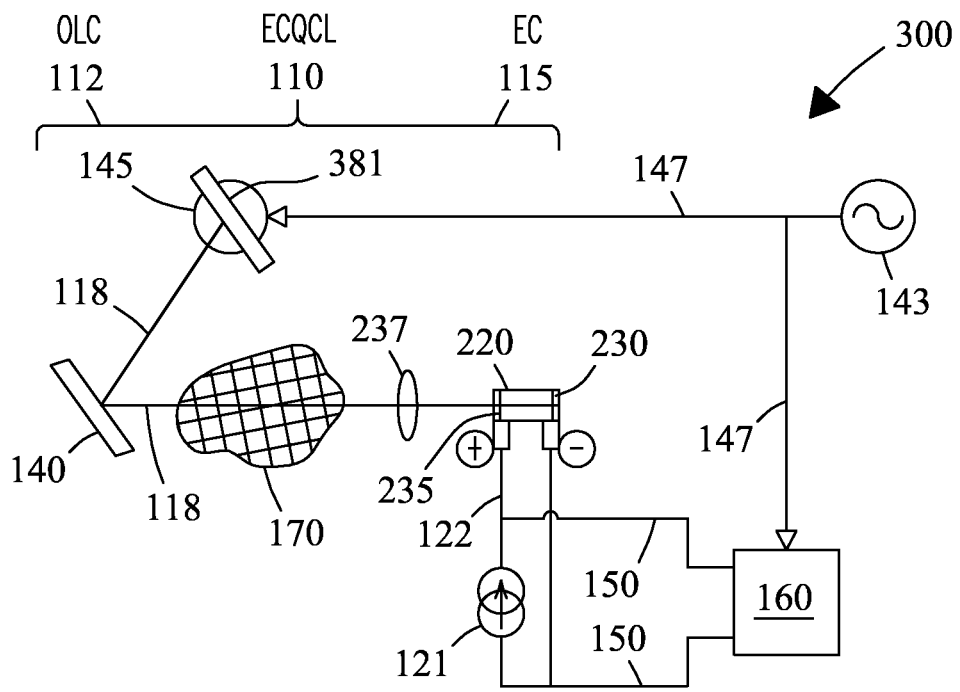
FIG. 3 shows a system for direct voltage detection and wavelength scanning of an unrestrained gas therein in a Littman-Metcalf ECQCL configuration, according yet another embodiment of the invention.

FIG. 3 shows an ECQCL voltage-mediated intra-cavity sensor (EVIS) 300 arranged in a Littman-Metcalf configuration. EVIS 300 may operate as a chemical sensor incorporated within an optical source. EVIS 300 may include an ECQCL 110 comprising a QCL device 220 with a high-reflectance mirror coating 230 and anti-reflection coating 235, focusing lens 237, a wavelength-selective element or device 140 such as an optical grating, an etalon, or an interferometer, and external mirror 381. Optical laser cavity (OLC) 112 in which an ECQCL mode 118 (or laser mode) exists is defined by these same items: QCL 220, optical grating 140, and external mirror 381. External cavity (EC) 115 is that part of the laser cavity 112 external to QCL device 220. ECQCL mode 118 is common to both QCL device 220 and EC 115. External mirror 381 may further be mounted on an actuator 145 that tunes the wavelength of ECQCL 110. EVIS 300 may also include a signal-generating device 143 that supplies actuator 145 with a scanning signal 147. Scanning signal 147 may provide rotation of external mirror 381, e.g., in a periodic manner. EVIS 300 may further include a current controller 121, which supplies QCL 220 with current 122. Compliance voltage 150 appearing across QCL 220 (and thus simultaneously across current controller 121) may be monitored by a measurement system 160 which may include amplifiers, mixers, filters, and computers or CPUs, but is not limited thereto. Compliance voltage 150 is preferably recorded simultaneously with scanning signal 147 and displayed with respect to, or processed as a function of, scanning signal 147. Presence of an analyte 170 in external cavity 115 of ECQCL 110 can be the result of their natural presence (i.e., passive introduction) in ambient air pervading ECQCL 110, or may be the result of deliberate introduction into optical laser cavity 112, e.g., in a gas stream, in a gas sample, or by another means. Analytes 170 in external cavity 115 of ECQCL 110 cause changes to ECQCL optical mode 118, which in turn cause changes in compliance voltage 150 detected across QCL 220, e.g., as detected by measurement system 160. Analytes 170 are thus detected by observing (or registering) changes in compliance voltage 150.

Figure 4:
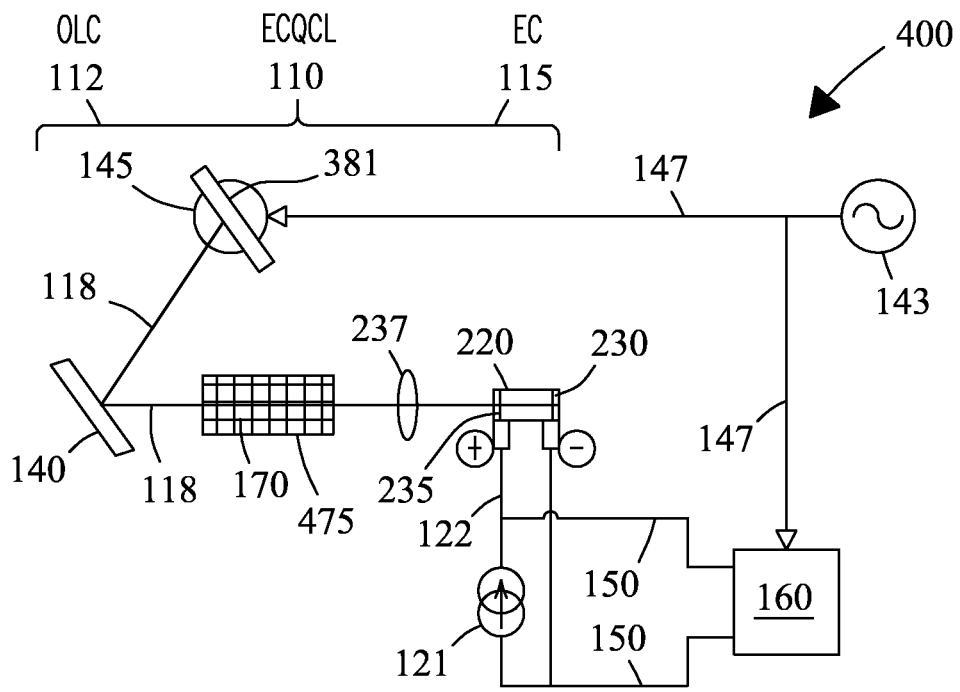
FIG. 4 shows a system that includes a gas cell configured for direct voltage detection and wavelength scanning of a gas contained within the gas cell in a Littman-Metcalf ECQCL configuration, according still yet another embodiment of the invention.

FIG. 4 shows an ECQCL voltage-mediated intra-cavity sensor (EVIS) 400 arranged in a Littman-Metcalf configuration. EVIS 400 may operate as a chemical sensor incorporated within an optical source. EVIS 400 differs from EVIS 300 in how analytes 170 are introduced into sensor 400. EVIS 400 may include an optical cell 475 into which analytes 170 are introduced. Optical cell 475 may be a gas cell, a flow cell, an optical cavity, or a multipass cell such as a Herriott cell or a White cell.

Figure 5:
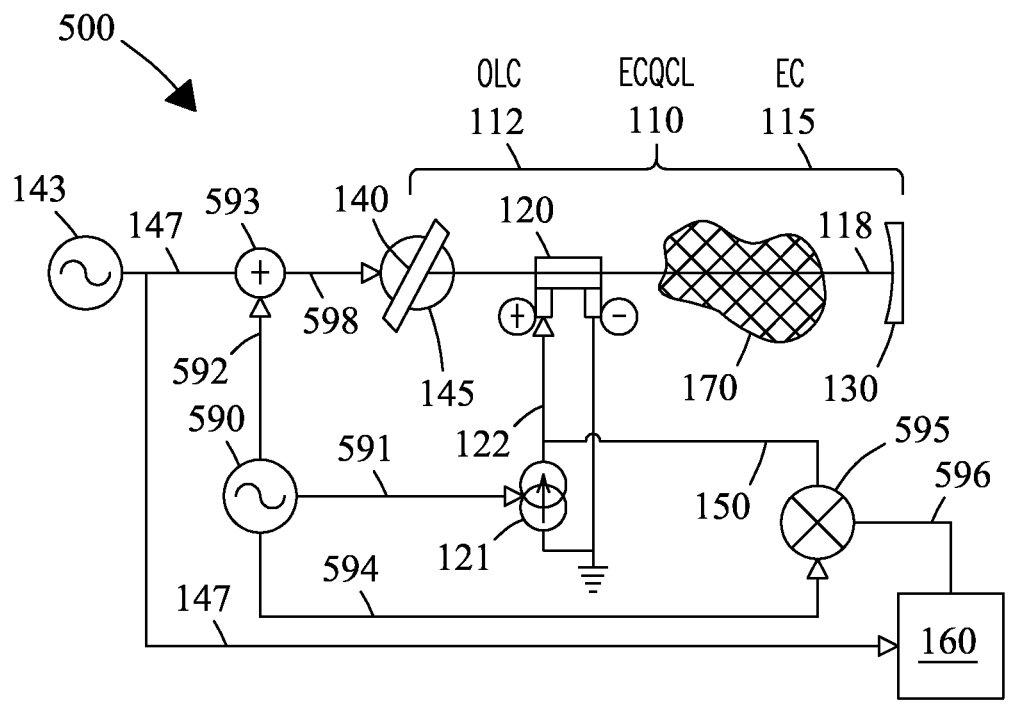
FIG. 5 shows a system employing demodulated voltage detection for wavelength scanning and modulation in a Littrow ECQCL configuration, according to yet another embodiment of the invention.

FIG. 5 shows a modulated ECQCL voltage-mediated intra-cavity sensor (EVIS) 500 arranged in a Littrow configuration. EVIS 500 may be identical to EVIS 100 (FIG. 1) in its optical configuration. EVIS 500 may include an ECQCL 110 and an associated optical laser cavity (OLC) 112 in which ECQCL mode 118 exists. ECQCL 110 and optical laser cavity (OLC) 112 may be defined by: external mirror 130, optical grating 140, and QCL device 120. External cavity (EC) 115 may be that part of optical laser cavity (OLC) 112 external to QCL device 120. ECQCL mode 118 may be common to both QCL device 120 and EC 115. EVIS 500 may include a first signal-generating device 143 that supplies actuator 145 with a scanning signal 147 via output signal 598 from summing device 593. Scanning signal 147 can provide rotation of optical grating 140, e.g., in a periodic manner. EVIS 500 may further include a current controller 121, which supplies QCL 120 with current 122. EVIS 500 may also include a second signal-generating device 590, which may provide modulation signal 591 to current controller 121, which may modulate current 122 in amplitude, which may in turn modulate ECQCL optical mode 118 within ECQCL 110 in amplitude, wavelength, or both amplitude and wavelength. Modulation signal 592 from second signal-generating device 590 may be added to scanning signal 147 through a summing device 593, the output signal 598 from which may modulate the motion of actuator 145 and in turn modulate ECQCL optical mode 118 within ECQCL 110, e.g., in amplitude, wavelength, or both amplitude and wavelength.

Modulation signals 591 and 592 may be used simultaneously to respectively modulate current 122 and motion of actuator 145. Modulation signals 591 and 592 can independently be of arbitrary waveform and wavelength. Summing device 593 can be an active device such as an amplifier or a summing buffer, or can include passive devices such as resistors, capacitors, and inductors, or can include direct connections between conductors. Further, summing device 593 can be external and separate from signal-generating device 143 and actuator 145, or can be internal to one of signal-generating device 143 or actuator 145. Compliance voltage 150 appearing across QCL 120 (and thus simultaneously across current controller 121) may be demodulated by demodulator 595 using a reference signal 594 derived from second signal-generating device 590. Reference signal 594 may be at a frequency corresponding to an integer or rational multiple of either the frequency of modulation signal 591 or modulation signal 592, or an integer or rational multiple of the product, sum, or difference of the frequencies of modulation signals 591 and 592. Output 596 of demodulation device 595 is a demodulated compliance voltage 596. Demodulated compliance voltage 596 may be monitored by a measurement system 160 which may include: amplifiers, mixers, filters, and computers or CPUs, but is not limited thereto. Demodulated compliance voltage 596 may be recorded simultaneously with scanning signal 147, and displayed with respect to, or processed as a function of, scanning signal 147. Presence of an analyte 170 or multiple analytes 170 in the external cavity 115 of ECQCL 110 can be a result of their natural presence (i.e., passive introduction) in ambient air pervading ECQCL 110, or may be a result of deliberate introduction into optical cavity 112, e.g., in a gas stream, in a gas sample, or by another means. No limitations are intended. Analytes 170 in external cavity 115 of ECQCL 110 may cause changes to ECQCL optical mode 118, which in turn may cause changes in compliance voltage 150 and thus the demodulated compliance voltage 596 detected by measurement system 160. Analytes 170 may thus be detected by observing or registering changes in the demodulated compliance voltage 596.

It should be understood that modulation methods and systems described with reference to EVIS 500 are independent of the optical configuration. While EVIS 500 has been described herein based on the optical configuration of EVIS 100, other embodiments could equally well be based on embodiments 200, 300, 400, or indeed other embodiments of the present invention. Thus, no limitations are intended.

Figure 6:
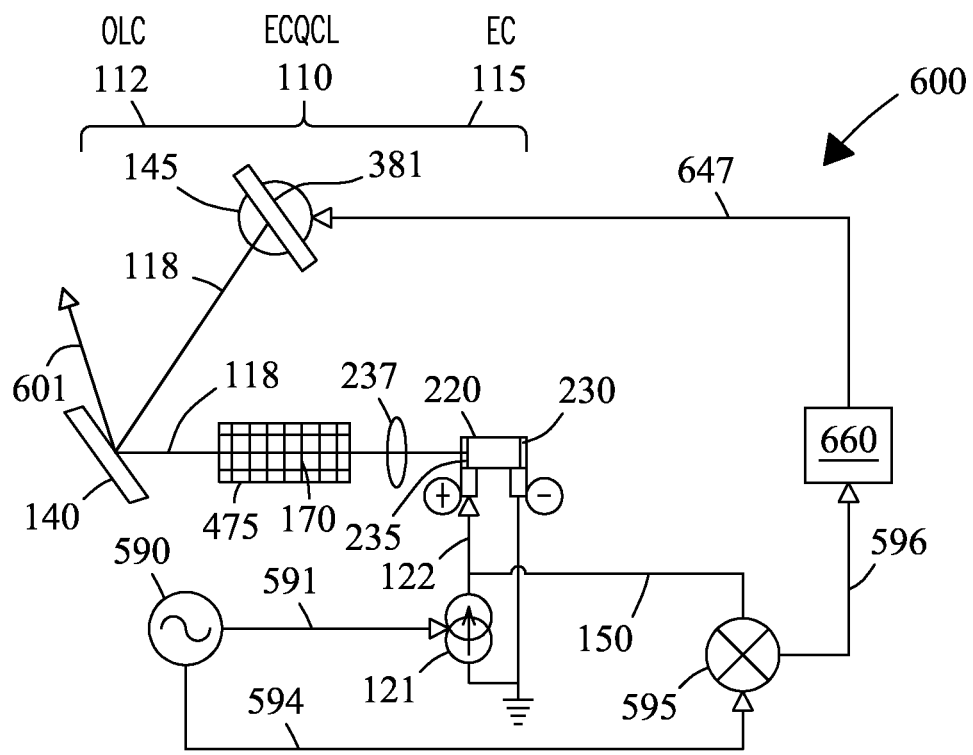
FIG. 6 shows a system that includes a separate demodulation device and control device for direct voltage detection and wavelength stabilization in a Littman-Metcalf ECQCL configuration, according still yet another embodiment of the invention.

FIG. 6 shows an ECQCL voltage-mediated intra-cavity sensor (EVIS) 600 arranged in a Littman-Metcalf configuration. Sensor 600 may also be used as a wavelength-stabilized light source. In some embodiments, EVIS 600 may not employ a flow-through cell or interaction region, but may continuously interrogate analyte 170, e.g., in a gas cell 475 or other fixed gas volume 475. EVIS 600 may include an ECQCL 110 that includes a QCL device 220 with a high-reflectance mirror coating 230 and anti-reflection coating 235, focusing lens 237, a wavelength-selective element or device 140 such as an optical grating 140, and an external mirror 381. Optical laser cavity (OLC) 112 in which a ECQCL mode 118 (or laser mode) exists may be defined by the following items: QCL device 220, optical grating 140 and external mirror 381. EVIS 600 may generate an output beam 601 that is distinct from ECQCL mode 118. ECQCL mode 118 may be common to both QCL device 220 and EC 115. External cavity (EC) 115 may be that part of laser cavity 112 external to QCL device 220. Fixed gas volume 475 may be considered a part of EC 115. Fixed gas volume 475 can be the entire volume of EC 115, of ECQCL 110, a simple gas cell, a flow cell, an optical cavity, or a multipass cell such as a Herriott cell or a White cell. External mirror 381 may be further mounted on an actuator 145 that tunes the wavelength of ECQCL 110. EVIS 600 may further include a current controller 121, which supplies QCL 220 with current 122. EVIS 600 may also include a signal-generating device 590 which provides modulation signal 591 to current controller 121 to modulate current 122, e.g., in amplitude, which in turn may modulate ECQCL optical mode 118 within ECQCL 110, e.g., in wavelength. Modulation signal 591 can be of arbitrary waveform and frequency. Compliance voltage 150 appearing across QCL 220 (and thus simultaneously across current controller 121) may be demodulated by demodulator 595 using a reference signal 594 derived from signal-generating device 590. Reference signal 594 may be at a frequency corresponding to an integer multiple or a rational multiple of the frequency of modulation signal 591. A demodulated compliance voltage signal (or error signal) 596 may be passed to control system 660. Control system 660 can include: amplifiers, servos, filters, and computers or CPUs, but is not limited thereto. Control system 660 may drive actuator 145 via control signal 647 to alter the wavelength of ECQCL 110 to keep it coincident with a selected molecular absorption line or feature of the analytes 170. Control system 660 may move the wavelength of ECQCL 110 rapidly between at least two molecular absorption lines or features of one analyte 170 or of multiple analytes 170. In this way, EVIS 600 may be wavelength-stabilized to one or more molecular absorption lines of a single analyte 170 or of multiple analytes 170. Output beam 601 may thus be coincident in wavelength with molecular absorption features of analytes 170.

Figure 7:
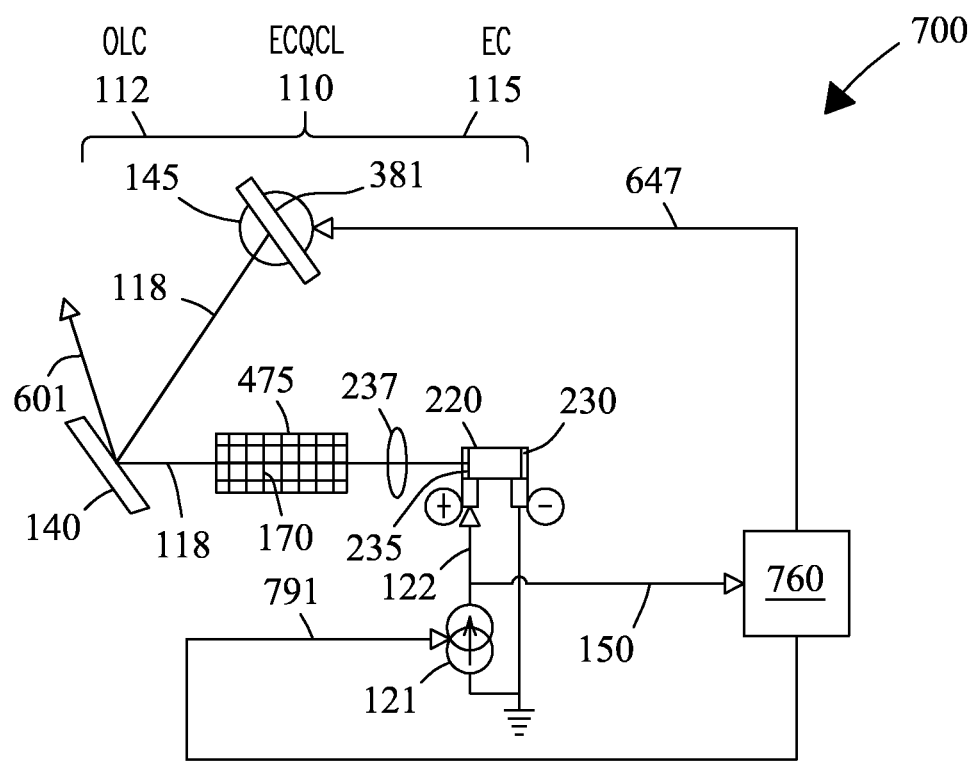
FIG. 7 shows a system that includes a combined demodulation device and control device for direct voltage detection and wavelength stabilization in a Littman-Metcalf ECQCL configuration, according still yet another embodiment of the invention.

FIG. 7 shows an ECQCL voltage-mediated intra-cavity sensor (EVIS) 700 arranged in a Littman-Metcalf configuration. Sensor 700 may be used as a wavelength-stabilized light source. EVIS 700 differs from EVIS 600 in how compliance voltage 150 is processed. Compliance voltage 150 appearing across QCL 220 (and thus simultaneously across current controller 121) may be measured by a control device or system 760. Control system 760 may include, e.g., mixers, amplifiers, signal generators, digital controllers, and computers or CPUs, but is not limited thereto. Control system 760 can alter current 122 passed to QCL device 220 from current controller 121 via a control signal 791. Control system 760 can also alter the wavelength tuning of ECQCL 110 via an actuator 145 and control signal 647. In this way, control system 760 can vary current 122 and/or wavelength tuning of ECQCL 110 in order to locate, identify, and stabilize ECQCL 110 to one or more molecular absorption lines or features of the at least one analyte 170. Control system 760 can also move the wavelength of ECQCL 110 rapidly between at least two molecular absorption lines or features of one analyte 170, or of multiple analytes 170. In this way, EVIS 700 may be wavelength-stabilized to one or more molecular absorption lines of at the least one analyte 170. In this way, output beam 601 may be coincident in wavelength with molecular absorption features of analytes 170.

Mathematical Functions

Mathematical functions described herein can include, but are not limited to, e.g., single value functions, binary functions, multiplication functions, multiplication by constant value functions, division functions, square-root functions, linear functions, polynomial functions, raising to mathematical (numerical) powers functions, exponential functions, logarithmic functions, trigonometric functions, binomial functions, and combinations of these.

Laser Measurements

Laser measurements described herein may include, but are not limited to, e.g., absorption measurements, fluorescence measurements, reflection measurements, distance measurements, phase measurements, interferometric measurements, temperature measurements, density measurements, and combinations of these.

Laser Spectra

Laser spectra described herein may include, but are not limited to, e.g., absorption spectra, fluorescence spectra, reflection spectra, distance spectra, phase spectra, interferometric spectra, temperature spectra, density spectra, and combinations of these.

Sweeping of Laser

"Sweeping" or "sweeping a laser" as these terms are used herein may refer to continuous tuning of a laser wavelength, or may refer to a piece-wise tuning of a laser wavelength where the wavelength may be set to specific wavelength values for a selected time period or for selected time periods.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

What is claimed is:

1. A method for stabilizing a wavelength of an external cavity laser (ECL), comprising:
   supplying a drive current to a laser device disposed within the ECL;
   modulating the operating wavelength of a laser mode of the ECL at a preselected modulation frequency, waveform, and amplitude when at least one analyte is present in the external cavity of the ECL;
   setting an average operating wavelength of the ECL to a value corresponding to an absorption feature of the at least one analyte;
   measuring a compliance voltage developed across the laser device;
   demodulating the compliance voltage at a preselected demodulation frequency, waveform, and amplitude to obtain an error signal;
   passing the error signal to a control member;
   applying an output of the control member to at least one wavelength-selective element within the external cavity of the ECL to form a feedback loop that acts on the operating wavelength of the ECL; and
   adjusting the gain, phase, and bandwidth of the control member to stabilize the feedback loop and the operating wavelength of the ECL.

2. The method of claim 1, wherein the control member is a servo-controller that includes at least one member selected from the group consisting of: amplifiers, filters, limiters, integrators, differentiators, filters, notches, computers, delays, and combinations thereof.

3. The method of claim 1, further including positioning the feedback loop such that the operating wavelength of the ECL is locked to a selected absorption feature of the at least one analyte.

4. The method of claim 1, wherein the at least one analyte includes a gas, a liquid, a solid, a plasma, or combinations thereof.

5. The method of claim 1, wherein the at least one analyte fills the external cavity of the ECL.

6. The method of claim 1, wherein the at least one analyte is contained within a gas cell disposed within the external cavity of the ECL.

7. The method of claim 1, wherein modulating the wavelength includes modulating the drive current to the laser device within the ECL.

8. The method of claim 1, wherein modulating the wavelength includes modulating with at least one wavelength-selective element disposed within the external cavity of the ECL.

9. The method of claim 1, wherein modulating the operating wavelength and setting the operating wavelength employ the same wavelength-selective element within the external cavity of the ECL.

10. The method of claim 1, wherein modulating the operating wavelength and setting the operating wavelength employ distinct wavelength-selective elements within the external cavity of the ECL.

* * * * *